United States Patent
Scott et al.

(10) Patent No.: US 8,096,304 B2
(45) Date of Patent: Jan. 17, 2012

(54) HEAD POSITIONING AID

(76) Inventors: Jane Scott, Twin Falls, ID (US); David Scott, Sedalia, CO (US); Julianne Heath, Wellington, CO (US)

(*) Notice: Subject to any disclaimer, the term of this patent is extended or adjusted under 35 U.S.C. 154(b) by 1044 days.

(21) Appl. No.: 11/957,383

(22) Filed: Dec. 14, 2007

(65) Prior Publication Data
US 2009/0151731 A1    Jun. 18, 2009

(51) Int. Cl.
*A61F 11/00* (2006.01)
*A42B 1/00* (2006.01)

(52) U.S. Cl. .......... 128/857; 602/17; 2/410; 5/655; 5/636

(58) Field of Classification Search ......... 128/97.1, 128/845, 857; 2/171, 173.5, 195.8, 201, 2/202, 209.13, 410, 204; 446/27; 602/17; 5/637, 643, 655, 603, 622, 636; 66/170, 66/200
See application file for complete search history.

(56) References Cited

U.S. PATENT DOCUMENTS

| | | | | |
|---|---|---|---|---|
| 1,582,812 A * | 4/1926 | Avin | ................ | 2/195.7 |
| 4,141,229 A * | 2/1979 | Sharpe | ................ | 66/171 |
| D339,668 S * | 9/1993 | Ochs | ................ | D2/872 |
| 6,954,954 B2 * | 10/2005 | Stelnicki | ................ | 5/655 |
| 7,153,284 B2 | 12/2006 | Argenta | | |
| 7,430,765 B2 * | 10/2008 | Brown et al. | ................ | 2/202 |
| 7,566,313 B1 * | 7/2009 | Argenta | ................ | 602/17 |
| 7,761,933 B2 * | 7/2010 | Pham | ................ | 2/410 |
| 2006/0185055 A1 * | 8/2006 | DeWitt | ................ | 2/111 |
| 2007/0199151 A1 * | 8/2007 | Brown et al. | ................ | 5/655 |
| 2010/0252054 A1 * | 10/2010 | Slatten | ................ | 128/845 |

FOREIGN PATENT DOCUMENTS
AU         2006201877 A1 * 11/2007

* cited by examiner

*Primary Examiner* — Patricia Bianco
*Assistant Examiner* — Kari Petrik
(74) *Attorney, Agent, or Firm* — Kyle W. Rost

(57) ABSTRACT

A head-positioning aid for treating or preventing plagiocephaly and torticollis is formed of a soft, compliant beanie-style cap. A soft and pliable deflector is attached to the beanie cap and extends downward from near the apex to near the lower edge of the cap. The cap is applied on an infant's head in an orientation to place the deflector at any required position about the circumference of the head. The cap and deflector are united by themed indicia designed to bring family acceptance of the cap to promote acceptance and thereby support long term usage, as may be required.

10 Claims, 8 Drawing Sheets

HEAD POSITIONING AID

BACKGROUND OF THE INVENTION

1. Field of the invention

The invention generally relates to beds and to support for a user's body or a part thereof. More specifically, the invention discloses a support especially adapted to the needs of an infant by providing a head covering that incorporates a positioning aid.

2. Description of Related Art Including Information Disclosed Under 37 CFR 1.97 and 1.98

Infants often are placed in their own beds or cribs, where they are left alone for sleep. At very young age, due to physical immaturity, an infant is unable to roll over. In addition, an infant has weak muscles supporting head position, such that a very young or premature infant may only have only limited ability to change even his or her head position. Consequently, the position in which he is placed often will remain the infant's sleeping position until someone else repositions him. From birth to about nine months of age, an infant's head position and sleeping position can be outside his own control.

Plagiocephaly is a condition characterized by a flattening of one side of the skull. This condition might arise when an infant is allowed to lie on his back a great deal of the time. Thus, the condition also is referred to as positional plagiocephaly. Although sleeping position seems to be a chief cause, the condition also might arise when an infant is left for a long time in any position where his head rests against a flat surface. As an example, an infant in a car seat might rest or hang his head consistently to one side. Torticollis is a sometimes-related condition characterized by asymmetry in the neck muscles, which can contribute to causes of positional plagiocephaly.

The treatment for positional plagiocephaly is to reposition the infant from time-to-time during his sleep periods. At one time, it was recommended to place the infant on his stomach, which readily allowed his head to be varied between right and left. However, a front sleeping position is suspected of contributing to sudden infant death syndrome (SIDS). Consequently, the current recommendation from professional sources is that infants should sleep on their backs. A back sleeping position leads to less certain position of the infant's head and increased concern for positional plagiocephaly.

Positional plagiocephaly is addressed at two levels. The first level is prevention. Parents and other caretakers routinely receive advice to shift the infant's head position and to discourage sleeping on the back of the head. The second level is treatment, once the problem has become severe. Correcting a severe problem can require use of a helmet. Physical therapy also can be helpful. Both corrective treatments involve expense and might be a burden on the infant's family. However, prompt corrective action is both desirable and important, because the problem becomes permanent once the skull becomes firm, at about 9 months to 1 year. It would be desirable to have a safe, inexpensive, and easily applied precautionary device, primarily to assist at the preventative stage.

Recent patent literature proposes a variety of solutions. U.S. Patent Application Publication 2006/0185055 to DeWitt proposes that a prop be attached to an infant's torso garment, parallel to the spine, to cause the infant to face toward a selected side during sleep. U.S. Pat. No. 7,153,284 to Argenta proposes a hard headgear or helmet with a protruding deflector that can be located selectively over a flat spot on the infant's head, causing the infant's head to roll off the deflector. U.S. Pat. No. 6,954,954 to Stelnicki proposes a system of wedges and props to establish a sleeping position, coupled with a helmet or cap that receives pads at selected locations. The pads are configured to become elevating pillows that support the infant's head rather than encouraging the head to roll off the pillow.

Although the suggested solutions may have value in clinical settings or at the treatment stage rather than at the preventative stage, their use in the home may not be desirable or suitable. Professional sources recommend against regular use of any device that restricts movement of an infant's head. In addition, because an infant's brain and head are rapidly growing, stiff headgear and helmets should be used under regular professional supervision to avoid harmful restriction. Further, the proposed devices are typically large, awkward, and overly suggestive of clinical purpose, which may discourage their use in the home or family setting.

It would be desirable to combine a head positioning aid with a pliable, broadly sized cap, so that an infant can wear the cap with substantially no problem of exceeding size capacity. Similarly, it would be desirable for a head positioning aid to be a pliant pad so that the infant's head is mildly influenced toward a selected position without foreclosing other movement. One or more pliant pads on a soft cap can provide a suitable and versatile means for directing an infant's head during sleep and in other situations. Such a cap offers the possibility of baby-friendly configurations and can avoid having a clinical appearance. A parent may be pleased to have an infant wear such a friendly cap on a regular basis, both at home and on normal travels, because the appearance of the cap does not imply medical treatment or clinical purpose as found in other devices.

To achieve the foregoing and other objects and in accordance with the purpose of the present invention, as embodied and broadly described herein, the method and apparatus of this invention may comprise the following.

BRIEF SUMMARY OF THE INVENTION

Against the described background, it is therefore a general object of the invention to provide devices for preventing or treating conditions such as plagiocephaly or torticollis. Such devices should be suited for regular home use by the parent or caretaker for an infant. Little instruction about use should be necessary, and the device should need only ordinary care in order to function properly.

A specific object is to provide a directional aid for an infant's head during rest, wherein matters such as selection and use of a suitably sized device are subject to inherent safety review each time the caretaker applies the device.

According to the invention, an aid for positioning the head of a resting infant in order to treat or prevent plagiocephaly and torticollis is formed from a close-fitting cap, especially a beanie cap. The cap is constructed of compliant fabric and sized to be worn over the top of an infant's head and to allow the lower edge of the cap to be disposed near the height of the infant's ears. A pliable, longitudinally elongated deflector is attached to the cap from near the apex of the cap to at least near the lower edge. When the cap is applied on an infant's head with the deflector at a selected position about the circumference of the infant's head, the cap supports the deflector with sufficient control to maintain the deflector at the selected position to deflect the infant's head from reposing directly on the deflector.

A method of the invention is carried out by, first, forming a dome-shaped cap constructed of rib knit material. The cap is sized to fit an infant-sized head. The cap has an apex defined at the top of the dome shape and has a lower edge defined at the bottom of the dome shape. A major seam extends from the apex to near the lower edge. A longitudinally elongated, arcuate, pliable deflector is formed of a soft material. The deflector is located over the major seam. The deflector is attached to the cap by incorporating a minor portion of the deflector into the major seam to form a resulting positioning aid for positioning the head of a resting infant. An orientation is selected for applying the positioning aid to an infant's head by identifying a selected edge portion of the infant's head that the infant should not rest upon. The positioning aid is applied over the top of the infant's head while the deflector is positioned to overlie the selected edge portion of the infant's head.

The accompanying drawings, which are incorporated in and form a part of the specification, illustrate preferred embodiments of the present invention, and together with the description, serve to explain the principles of the invention. In the drawings:

DETAILED DESCRIPTION OF THE INVENTION

Figure 1:
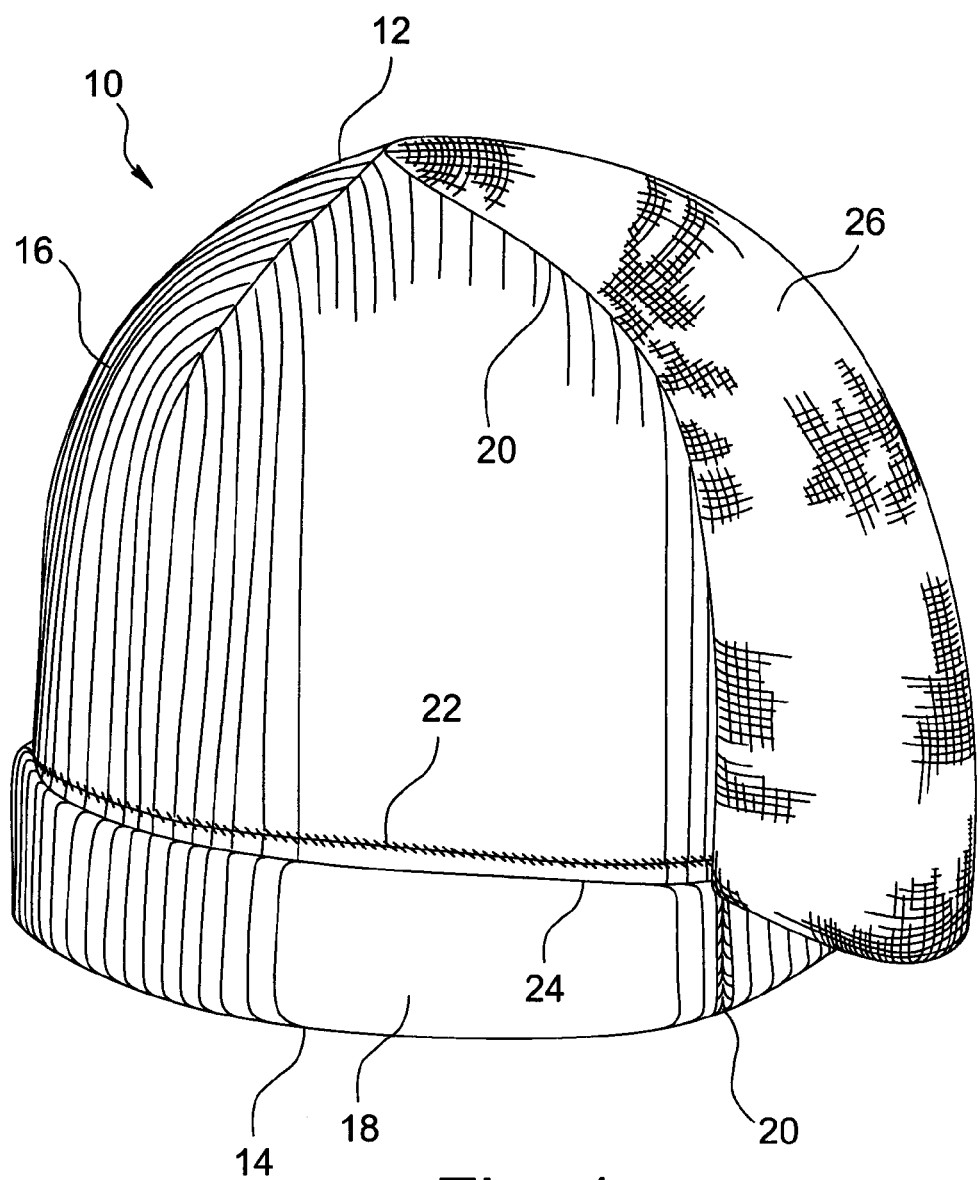
FIG. 1 is a right side elevational view of a head-positioning aid of the invention.

The invention is a head positioning aid 10 for use in guiding the head position of a resting infant. A premise of this invention is that having his head placed or guided in selected sleeping positions is helpful to the infant. At birth, an infant has little capability to support his own head. With only a small degree of instruction or even by empirical experience alone, parents and other caretakers learn that an infant requires his head to be supported in almost any situation. Thus, it may be observed that an infant's head tends to droop or fall whenever allowed to do so. An infant in a car seat or carrier may droop his head to a side, for lack of ability to move it to another position. An infant resting on a bed may appear to have his head better supported, but this appearance of better support can be deceptive. The infant might remain unable to move or turn his head from a single position of repose. The positioning aid 10 increases a caretaker's ability to adjust and control the resting position of infant's head.

Cranial asymmetry or localized flatness can result from the infant's head resting in the same position for too great a time. This type of problem might occur when an infant is allowed to sleep without changing his head position over a prolonged time. One side or position of the skull might become flat, resulting in the condition known as plagiocephaly. The head positioning aid 10 is useful both for preventing occurrence of plagiocephaly and for correcting this condition where it has occurred. Similarly, the positioning aid is useful for preventing and correcting occurrences of torticollis, involving asymmetry in the neck muscles.

The head positioning aid 10 is formed of a pliable base member, which may be similar to a skullcap, such as a stocking cap that fits around the upper portion of the skull. For purposes of description and not limitation, the preferred type of cap with pliable base is illustrated in the drawings and referred to herein as a beanie style cap 12. Such a beanie cap 12 should be soft, pliable, and stretchable. When worn, the cap is compliant to the wearer's head and evenly applies an elastic grip around the head.

Figure 2:
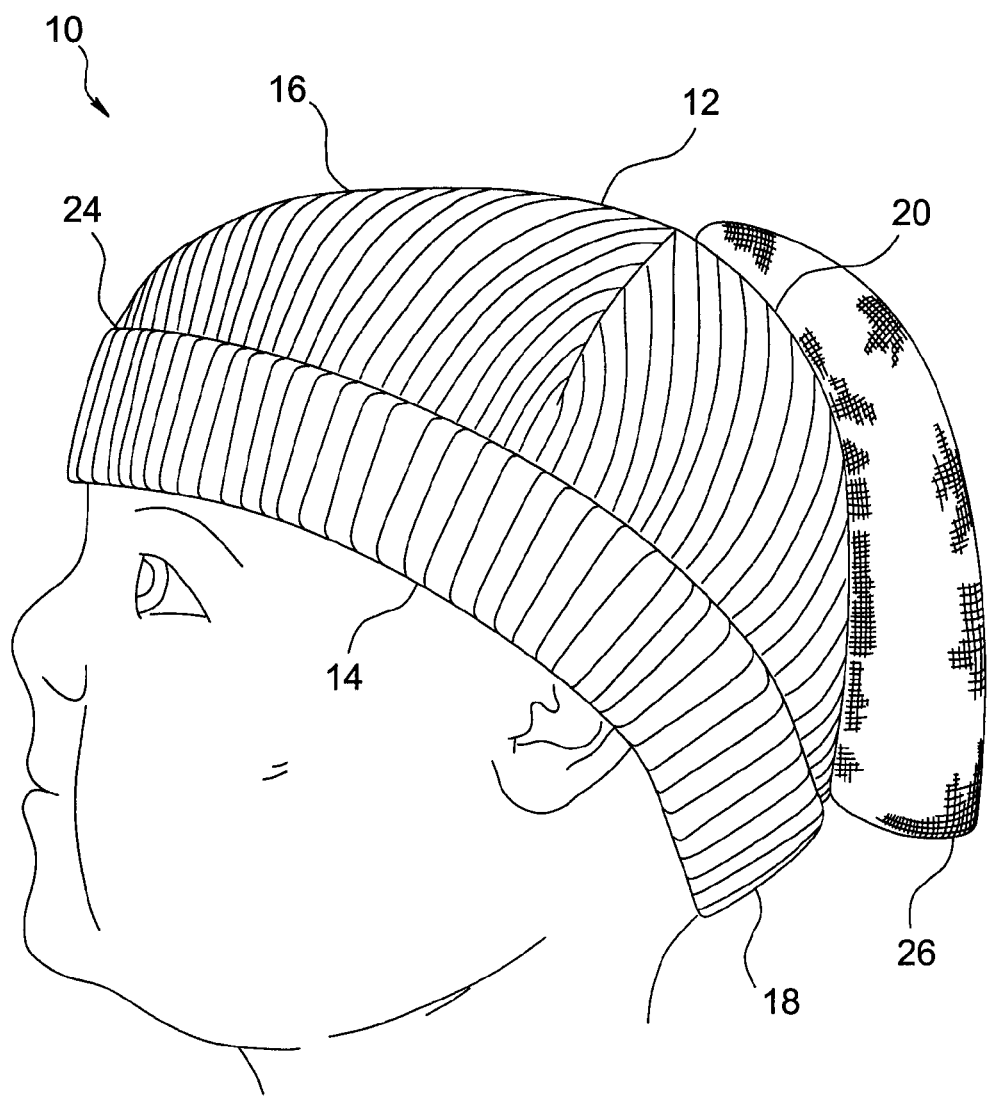
FIG. 2 is a right side elevational view of the head-positioning aid as typically applied to an infant's head.
Figure 3:
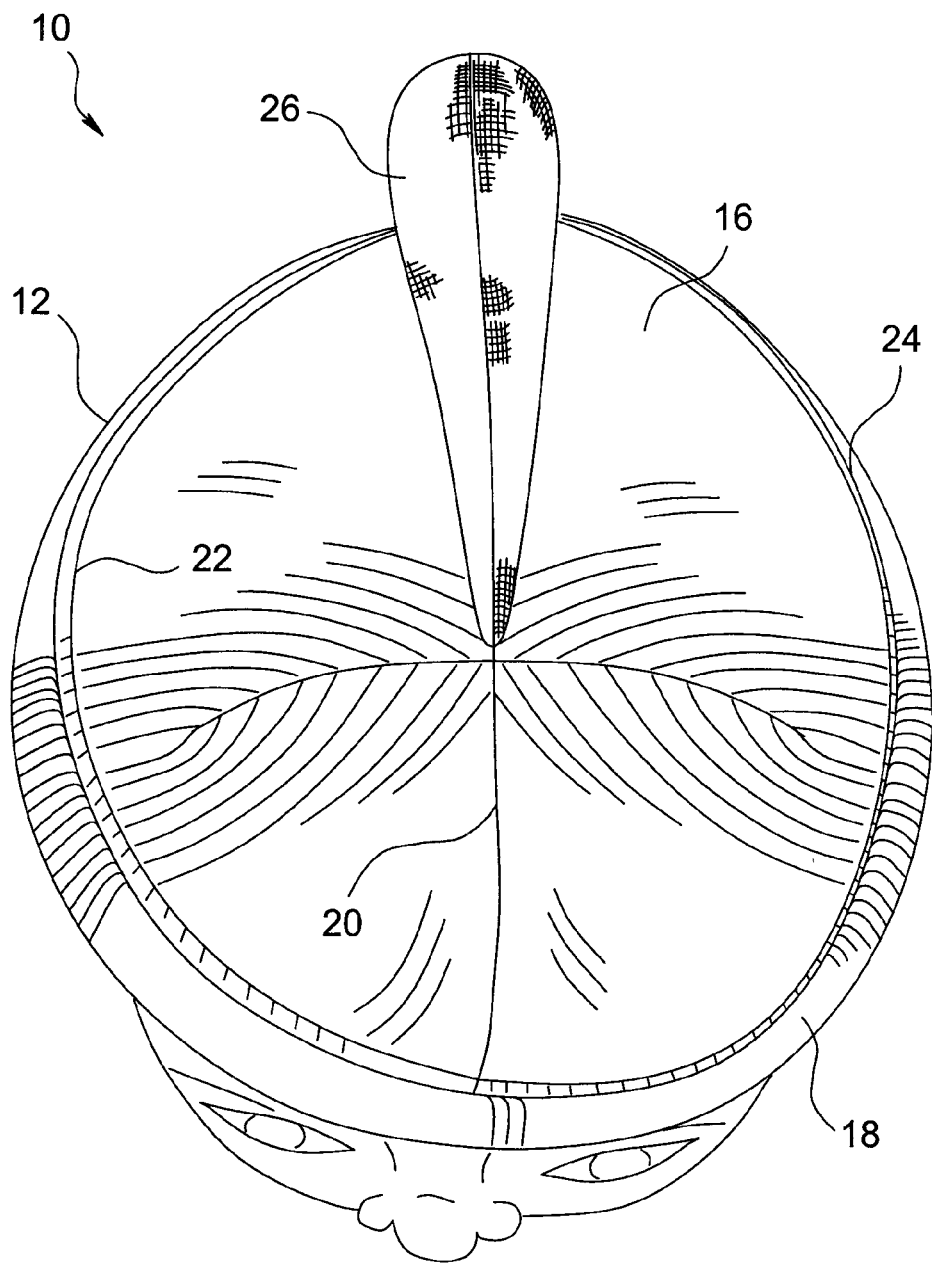
FIG. 3 is a top plan view of the head-positioning aid of FIG. 2.

FIGS. 1-3 illustrate a suitable example of a beanie cap 12 to be a tubular knit body that is shaped to encircle the infant's head. The tubular knit body has an apex at its top and has a bottom opening 14 providing conventional entry for the infant's head. The cap 12 may be formed of two subcomponents. A crown 16 defines the basic dome, which becomes a skull-fitting shell that fits from the apex of the hat to near the anticipated or typical height of the infant's ears. The stretch of a knit fabric provides considerable adjustment and variation in how far a cap can be pulled on, in use, over an infant's head.

Additional fabric control is established by use of a turn-up band 18 around the lower edge of the cap 12. A single or double-layer extension around the bottom of the crown 16 may be folded up to provide the conventional turn-up 18. The crown often is sized to end slightly above the typical location of an infant's ears, leaving room for the turn-up 18 between the bottom of the crown and the ear location. The dimension of the turn-up 18 can be adjustable so as to cover or uncover the infant's ears, as may be desired to accommodate ambient temperature. The turn-up band may be of fixed height, such as a double fabric layer or a folded up band that is sewn in place at seams to prevent unfolding. The apex of the crown 16, opposite from the turn-up band 18, may be closed by appropriate gathers or seams, which may include one or more major seams 20 bringing together substantial portions of the crown, or by any other technique forming a closed top of a cap.

The preferred style of beanie cap 12 is close fitting, so as to hug the top of the infant's head. A close fitting style is preferred in order to obtain resulting control of the fabric, despite the soft knit and stretchable nature of the fabric. A knit cap offers considerable stretching ability. A rib knit as illustrated in FIGS. 1-3 offers a large amount of stretch across the series of ribs. Where the knit ribs are oriented with alignment roughly between bottom edge and apex of the cap, the stretching ability is concentrated on the circumference or size of the cap. The knit fabric might be readily stretchable across the knit ribs by a factor of two or three and sometimes more. Lengthwise, or viewed as a top-to-bottom dimension of the cap, the knit ribs typically will stretch to a lesser degree, often to a factor of less that one and possibly to a factor of one-half.

A close fitting beanie cap 12 is at least slightly stretched across the knit ribs, automatically equalizing the stretch around the infant's head to achieve a comfortable, even fit. Certain structures in a beanie knit cap 12 and typically in other styles of cap can limit stretch. Seams are helpful in preventing or limiting unwanted stretch. Increasing the number of fabric layers tends to limit stretch or to increase the force level necessary to achieve a predetermined degree of stretch.

The knit cap 12 illustrated in FIGS. 1-3 controls stretch by the addition of the turn-up 18 and by the addition of a turn-up seam 22. The turn-up 18 can be formed of a band or ring formed with two layers of knit fabric. The ring can be formed of a single sheet of fabric that is folded up at initial fold edge 24 to form a band having two fabric layers. Opposite from the fold edge 24 are the two free edges of the band fabric. The two free edges are sewn together and to the lower edge of the crown 16, thereby attaching the turn-up 18 to the crown 16. The combination of the lower edge of the crown 16 with the two free edges of the turn-up band 18 defines the circumferential turn-up seam 22.

The resulting turn-up band 18 is formed of at least two layers of fabric. In addition, the double layers of fabric can be folded up near the mid-height of the turn-up 18, bringing folded edge 24 up to turn-up seam 22. The turn-up 18 is sewn in place to prevent unfolding. The turn-up 18 might be sewn in folded position by stitching it at two or more locations, such as at vertical major seams 20. As a result, the turn-up 18 consists of four layers of knit fabric and includes a circumferential seam 22 at the intersection with the crown 16. The turn-up 18 and the seam 22 serve as stretch control devices that help prevent loss of size and that contribute to fabric control, which benefits the head positioning function of the positioning aid 10.

The head positioning aid 10 is further formed of a soft, pliable deflector, which may be a stuffed deflector 26, mounted to the base member such as crown 16. A suitable deflector is formed of a longitudinally elongated cloth casing filled with a soft stuffing, batting, or the like. The casing can be filled and then closed by a seam. The approximate shape of the deflector is an arc or half crescent. As shown in FIGS. 1-3, the arc is preferred to be approximately a quarter circle or slightly less. The length of the arc may be greater than apparently needed, so as to widely distribute any pressure of the arc against the infant's head, when worn. The arc is sized to fit the expected curvature and dimensions of the cap 12. The arc is similar to the side curvature of the crown 16 when laid flat. With a properly designed crown 16 that should approximately fit an infant's head, the similar or matching arc of the deflector should fit comfortably against the infant's head.

A suitable method of mounting the deflector to the cap is by sewing a minor portion of the deflector into a major seam 20 of the cap. The cloth casing can be closed by an outwardly extending seam along one edge, which typically will be the edge juxtaposed to the beanie cap 12. This extending deflector seam can be inserted between two edges of the beanie fabric that are to be sewn together into a seam. The resulting seam attaches the deflector into the seam of the beanie cap. The deflector becomes a fixed part of the cap, with the majority of the deflector extending outwardly from the seam. The attaching seam containing the minor portion of the deflector serves as a fabric control mechanism. Other methods of attaching the deflector to the cap may be used, including varieties of bonding or the use of adhesives. These and other methods also provide a mechanism for fabric control that increases stiffening at the attachment interface.

In particular, the cap might be formed to two mirror-image halves sewn together at a single, central, front-to-rear seam. The deflector can be sewn into this central seam, or the deflector can be sewn into another major seam such as a seam extending from apex to lower edge or the crown 16. The arc of the deflector might conform to the curvature of the cap at the chosen seam line 20. Matching the arc to the seam line 20 will allow the cap and deflector to be packaged in a configuration with the cap pressed flat at the chosen seam 20, thereby allowing the deflector to be packaged while lying in approximately its natural arc.

The stuffed deflector 26 is arranged as an extension from the outer surface of the generally skull shaped or dome shaped configuration of the cap 12. Preferably, the stuffed deflector follows the surface of the cap 12 at the theoretical intersection with a vertical plane bisecting the cap. As mentioned, this theoretical intersection might correspond to a major seam line 20. Thus, the desired orientation might place the stuffed deflector along a major seam 20 of the cap 12. The stuffed deflector might extend from the apex of the crown 16 to the turn-up seam 22 or top edge of the turn-up 18, covering an arc of about ninety degrees.

The stuffed deflector 26 extends outward from the outer surface of the cap 12 by a distance sufficient to assert a bias against the infant's rolling his head over the deflector. In the views of FIGS. 1-3, the deflector 20 may have a nominal thickness at the cap apex, increasing to an effective thickness near the lower edge of the cap, such as at the turn-up 18, of about two inches. The deflector is shaped as a deflector rather than as a pillow. Correspondingly, the side-to-side width of the deflector near its bottom, at the turn-up 18, is best less than the deflector's thickness. As an example, the width might be about one inch, or about one-half the deflector's thickness.

The deflector is filled with stuffing, which may be a soft stuffing so as to provide comfortable interaction with the infant's head. The stuffing should be sufficient in amount or in resulting firmness to continue to define a functional deflector when worn on an infant's head and when weighted with an infant's head resting on it or rolling over it. As a general guideline, the deflector should compress to no less than fifty percent of its uncompressed thickness when weighted under an infant's head.

While this guideline is approximate, it takes into account several practical factors. One practical factor is that an infant's head grows quickly between birth and age of nine months, such that the weight of an infant's head considerably increases during this period. Another practical factor is that the infant's musculature increases over this nine-month period. At birth, an infant has little musculature controlling the head, and a minor deflector height might be fully satisfactory. However, at nine months age, the musculature has increased and the infant is more able to assert his own head position. In this latter circumstance, the deflector must provide a positive deterrent to the head from resting directly on the deflector.

Still another practical factor is that the cap and deflector together remain a soft and pliable body. The deflector not only might crush under pressure but also might laterally roll or bend from its attachment to the cap. Particularly if the deflector is attached only at a seam line 20, a side-to-side pivot is increasingly likely as the head increases in weight and supporting musculature. The structure and firmness of the deflector should accommodate such anticipated changes and increased demands as the infant grows.

One of the advantages of using a beanie cap 12 as a base for the deflector is automatic and natural size evaluation that follows each time the cap is applied to the infant's head. The caregiver who applies the cap will experience an interaction of sensing the tightness of the fit as the cap is pulled onto the infant's head. A loose, stretched out cap will be detected as readily as a snug cap.

However, a further advantage is that even a snug cap retains inherent flexibility of cloth or knit fabric and distributes forces around the entire perimeter of the cap. As a result, little concern should be necessary that a cloth cap could restrain or overly press upon any limited area of the skull. A stretchable cloth cap is inherently safe and lends a desirable safety margin. Rather than requiring the caregiver to specifically investigate the fit of a hard headgear and to make a decision on which graduated size to select, as necessary with some other stiff devices, the beanie cap is self-adjusting over a considerable size range.

The head positioning aid 10 might be supplied with the beanie cap portion available in a basic size array, such as small, medium, and large. Over a typical nine-month period of use, head positioning aid 10 should require few replacements due to size issues. Correspondingly, the fabric construction of the head positioning aid 10 should enable this aid to be widely affordable and easily replaceable. Selecting a suitable size for an infant of any age becomes a non-technical decision. The decision can be correlated approximately with the infant's age, with a size recommendation on the cap or package such as size small up to two months, size medium up to six months, and size large up to nine months. The soft structure of the head positioning aid 10 allows compact storage, so that a cap is easily carried during travel, and spare caps require little storage space in the home, shop, or professional care facility.

Figure 4:
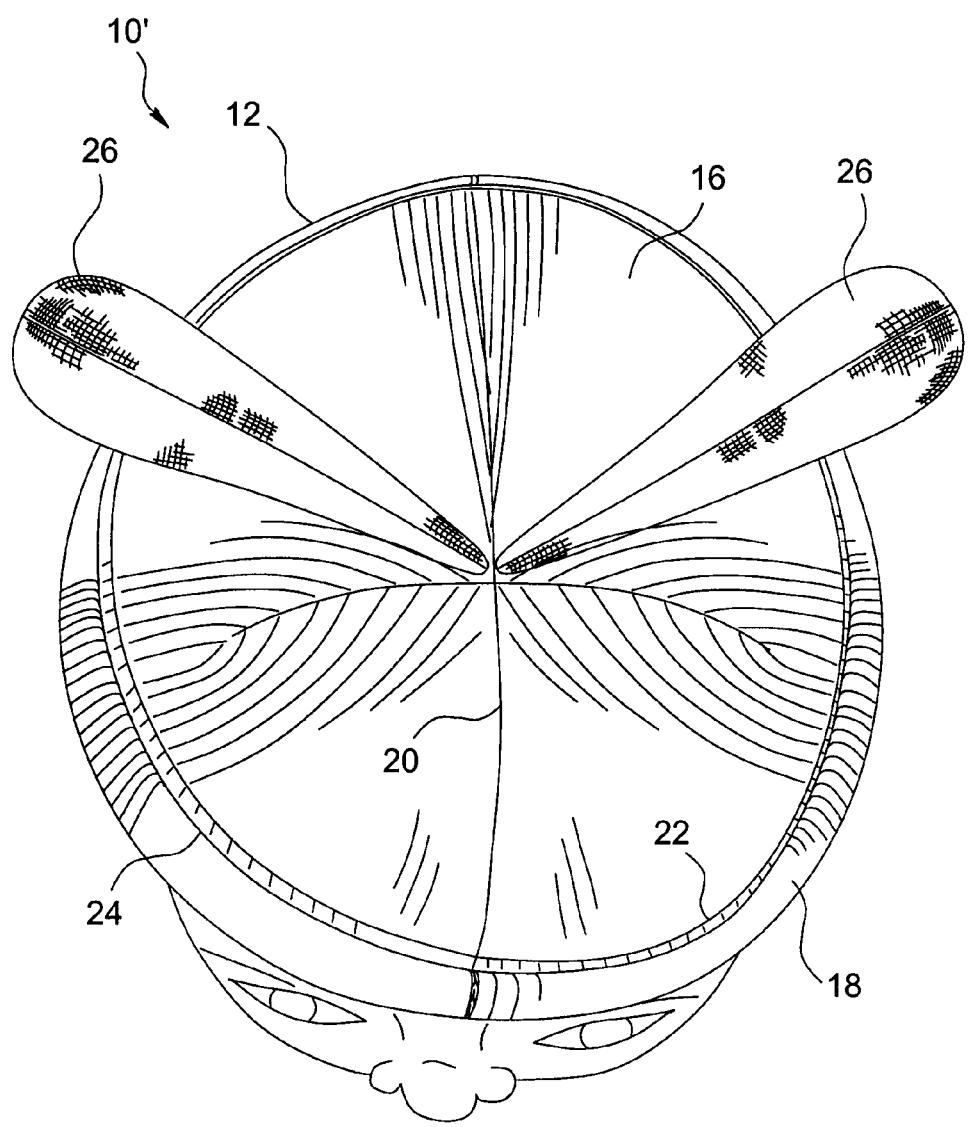
FIG. 4 is a view similar to FIG. 3, showing a modified embodiment of the head-positioning device.

FIG. 4 shows a modified embodiment of the head positioning aid 10'. The same numbers are used to identify elements similar to those previously described. In the modified embodiment, a plurality of deflectors 26 is present on a single beanie cap 12. As an example, two deflectors 26 might be separated by at least a quadrant of the cap. A suitable separation might be by an angle from about ninety degrees to about one hundred eighty degrees. A preferred separation angle is about one hundred twenty degrees. This embodiment can aid in positioning an infant's head in situations where the head is subject to greater uncontrolled movement. As an example, an infant riding in a car seat might find his head drooping from side-to-side with considerable freedom. A deflector 26 at each side can aid in turning the infant's head at whichever side it rests.

In any of the embodiments, the use of the positioning aid is similar. The beanie cap 12 is non-directional by inherent structure. The deflector 26 serves as the main positional marker. In many situations, the cap is applied with the deflector 26 centered to the rear, as shown in FIG. 3, or symmetrically arranged on each side of the head, as shown in FIG. 4. However, the beanie cap 12 can be worn with a deflector 26 at another, variably selected position, as required or suitable to the situation. A caregiver is able to vary the deflector's position by the non-technical method of readjustment of applying the cap 12 with the deflector 16 in a new, suitable orientation.

An aspect of treating an infant is to gain support and cooperation from parents or other caregivers. Particularly when a treatment lasts over a long time such as several months, and particularly when the treatment is preventative rather than corrective, it can be difficult to obtain long-term, consistent cooperation. Parents might tire of using a technically difficult device, and parents might become discouraged at using a device that does not conform to the warmth and happiness of a nursery setting.

The positioning aid 10 offers a high level of friendliness and compatibility with the infant and the nursery setting. The soft, cloth, knit cap structure is non-imposing and non-technical. In addition, a beanie cap 12 is a frequently worn item of infant wear, for warmth.

As an optional and supplemental step in offering an infant-friendly aid, the cap 12 and deflector 26 can be configured to include topical theme elements, especially theme elements relating to infant-friendly themes. FIGS. 5-8 illustrate suitable examples in which the cap 12 has been configured to convey an infant-friendly theme. By way of example and not limitation, an infant-friendly theme is one that relates to babies, children, family matters, nursery stories, fantasy, sports, nature, and the like. The infant may be unaware of the theme, but others around the infant will see and relate to the theme. In turn, the others around the infant will be influenced in their attitudes toward the infant and toward the use of the positioning aid 10. The deflector 26 is in the form of a three dimensional complementary object to the topical theme. The ability to conform the positioning aid 10 to a theme of infant or childhood relevance or adult/child interest provides an improved likelihood that caregivers will continue to employ the aid over a long term.

Figure 5:
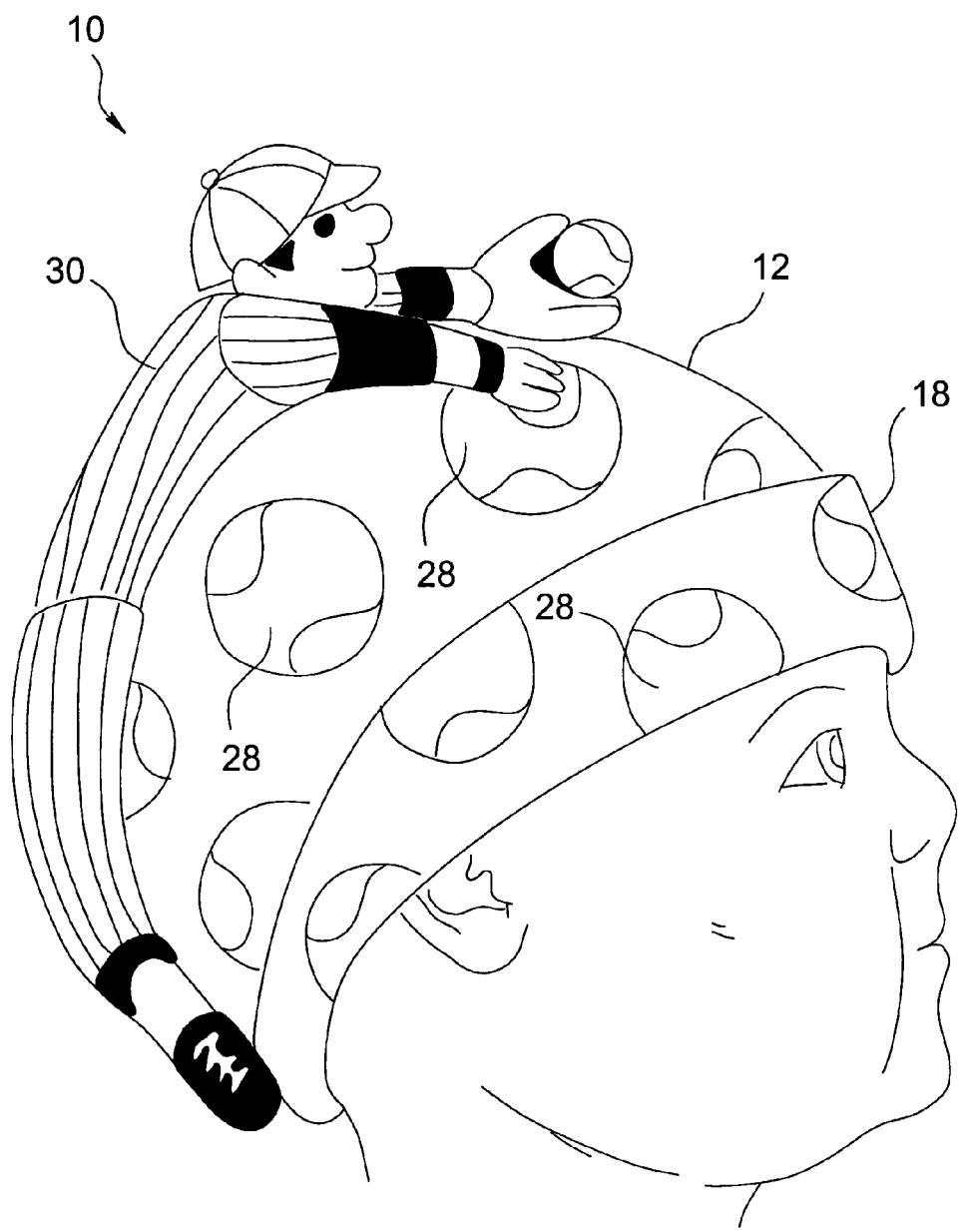
FIG. 5 is a left side elevational of the head-positioning aid as typically applied to an infant's head, showing a modification with first theme indicia.
Figure 6:
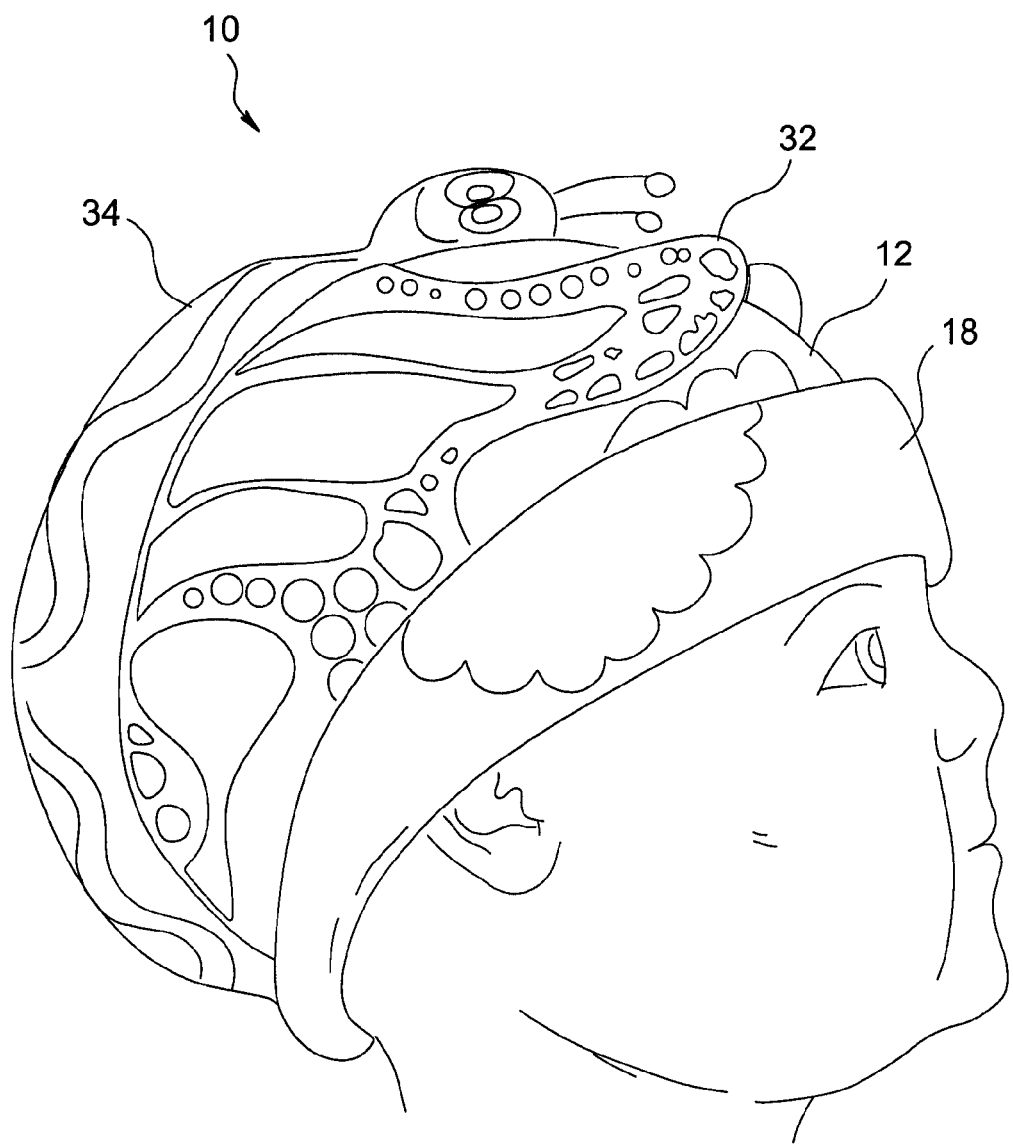
FIG. 6 is a view similar to FIG. 5, showing a modification with second theme indicia.
Figure 7:
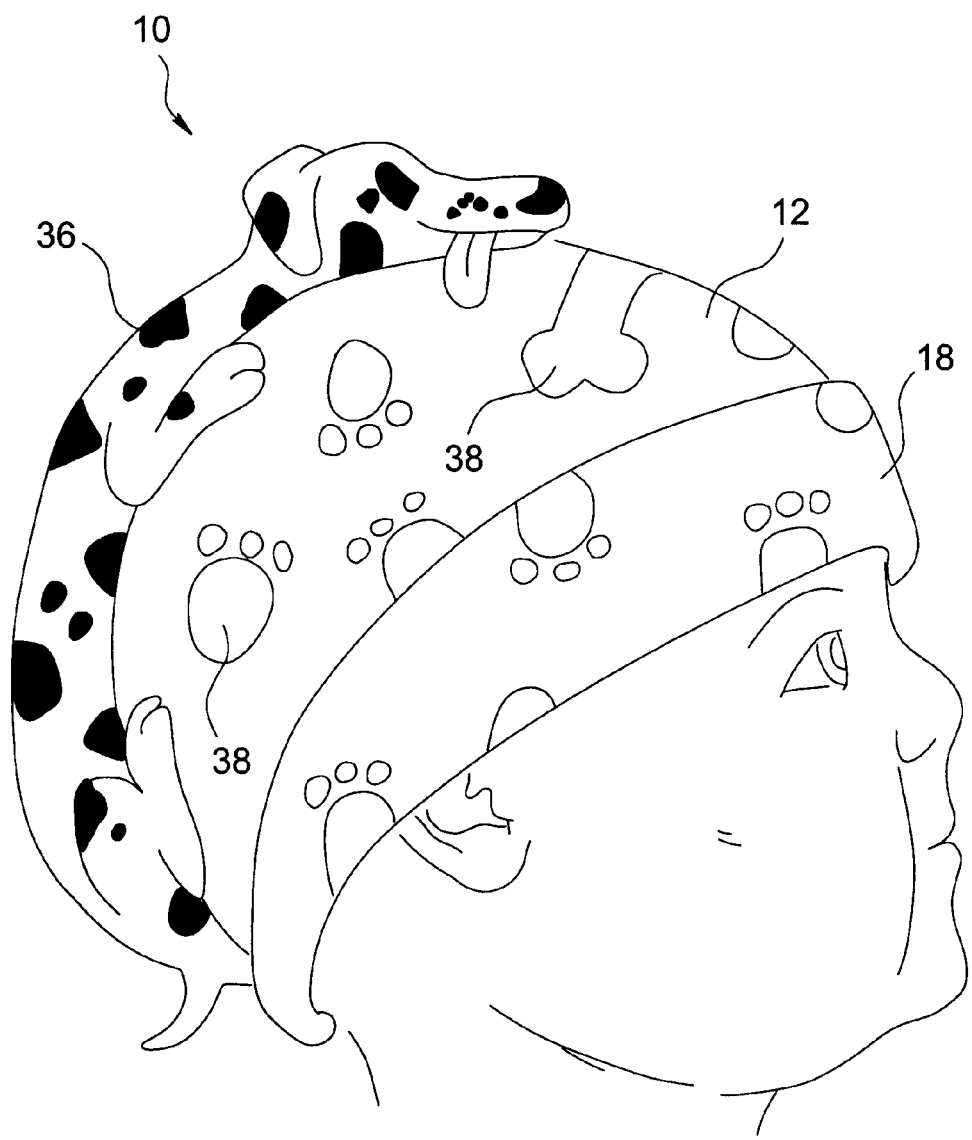
FIG. 7 is a view similar to FIG. 5, showing a modification with third theme indicia.
Figure 8:
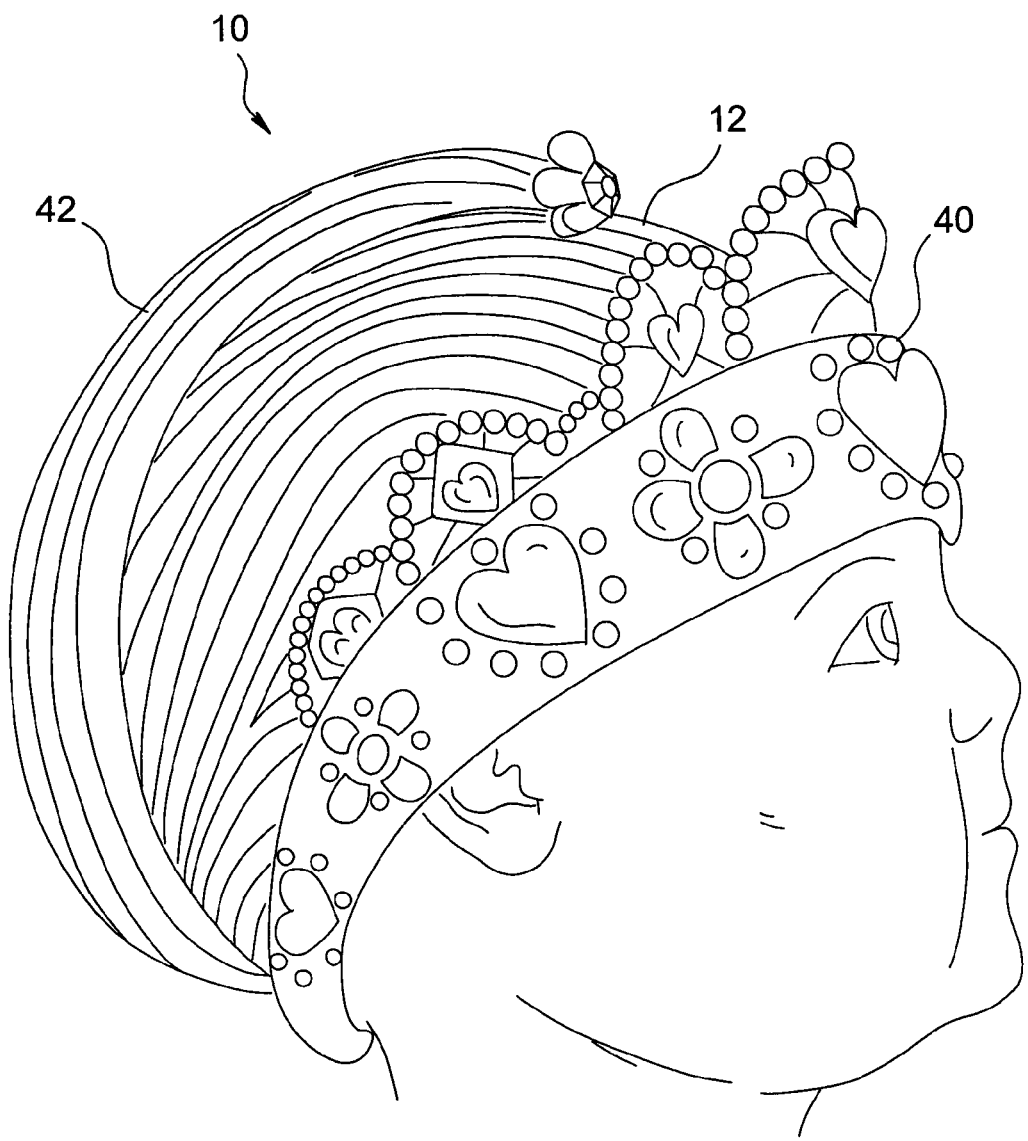
FIG. 8 is a view similar to FIG. 5, showing a modification with fourth theme indicia.

FIG. 5 shows a positioning aid 10 in which the cap 12 displays themed indicia related to sports, such as images 28 of baseballs. The deflector is configured as a sports player, in this case a baseball player 30 catching a baseball. The baseball player 30 is extended over the cap 12 to appear to be diving for a catch. The attractiveness of this theme and indicia, as well as those shown in FIGS. 6-8, is directed both to the patents and to other children. A child wearing this aid 10 should attract positive attention from both parents and other family members, which is important to the infant's acceptance and integration into the family. The means for treating or preventing a medical condition has been made into an attractive garment that has a good likelihood of being accepted by family members, with the result that the cap 12 is likely to be worn as long as needed. The example of a baseball theme is representative of other sports themes that could be applied. As a close parallel, the sports theme could have been football, showing football images on hat 16, with deflector configured as a football player catching a football in place of baseball player 30, but otherwise in a similar posture.

FIG. 6 shows a positioning aid 10 in which the cap 12 and themed indicia are integrated to form a unified object. The chosen object is a butterfly, with ornate wings 32 forming a part of the cap 12 and with the butterfly body 34 forming the deflector. Creatures with wings are suitable subject matter for the integrated indicia and deflector. Other suitable candidates include birds and winged insects.

FIG. 7 shows a positioning aid 10 in which the indicia on the cap follows an animal theme, but with integration of a deflector object complementary to the theme as suggested in FIG. 5. The chosen deflector object is a dog 36 in a lying position. The related theme indicia for display on the cap 12 are dog footprints and bones 38. Other animal themes might substitute a different household pet or wild animal.

FIG. 8 shows a positioning aid 10 in which the cap 12 and theme indicia relate to a person such as a character from nursery story or fantasy, or to a costume object closely associated with a character from nursery stories or fantasy stories. The chosen indicium is an integrated princess' crown. The ornate indicium of the cap 12 is a jeweled tiara 40, arranged primarily as the turn-up or extending from it. The deflector is an integrated portion of the crown body 42. Other fantasy or costume themes might substitute a different fantasy character or costume element.

As described, the head positioning aid 10 overcomes problems of overly complex and technically imposing devices for treating or preventing plagiocephaly or torticollis. The cap structure is easily understood and applied for clinical or home use. Parents and other home caregivers are presented with an effective and friendly aid 10 that can be used in family or in public with positive reception. Optional whimsical indicia and complementary deflector configurations further enhance the baby-friendly nature and acceptance of this aid.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

What is claimed is:

1. An aid for deflecting the head of a resting infant from reposing upon a preselected area of the head in order to treat or prevent plagiocephaly and torticollis, comprising:
a cap having an apex and lower edge, formed of compliant fabric and sized to be worn with said apex fitting over the top of an infant's head and to allow said lower edge of said cap to be disposed over the infant's ears;
a pliable longitudinally elongated deflector attached to said cap from near the apex of the cap to at least near said lower edge, wherein the deflector is more elongated between the apex and lower edge of the cap and is narrower a in transverse dimension such that the deflector is a positive deterrent to the infant's head from resting directly on the deflector; and
wherein when the cap is applied on an infant's head with said deflector positioned on said preselected area of the head for treating or preventing plagiocephaly or torticollis, the cap supports said deflector with sufficient control to maintain the deflector at the preselected area to deflect the infant's head from reposing directly on the preselected area.

2. The aid according to claim 1, wherein:
said cap is a beanie cap;
said compliant fabric forming said cap is a rib knit, arranged with ribs oriented between said lower edge and apex of the cap, such that fabric forming the cap is stretchable in circumference across the knit ribs by a greater degree than in the longitudinal dimension of said deflector;
the cap includes at least one major seam extending from the apex to near the lower edge; and
the deflector is attached to the cap by sewing into said at least one major seam;
whereby the orientation of ribs and attachment of the deflector to the major seam provide fabric control for stabilizing the position of the deflector with respect to the cap.

3. The aid according to claim 2, wherein said cap further comprises:
a turn-up band attached at said lower edge of the cap, defining at least two layers of said knit fabric;
whereby the turn-up band provides fabric control for stabilizing the position of the deflector with respect to the cap.

4. The aid according to claim 3, wherein the attachment of said deflector to said cap is located above said turn-up band.

5. The aid according to claim 1, wherein:
said deflector is formed of a cloth casing and a stuffing within said casing, establishing the pliability of the deflector.

6. The aid according to claim 1, wherein:
said cap is a beanie cap;
said deflector includes a lower portion thereof near said lower edge of said cap; and
said lower portion of the deflector is of selected width and selected thickness, wherein the selected thickness is at least twice the selected width.

7. The aid according to claim 1, wherein:
said cap carries indicia signifying a predetermined theme;
said deflector is configured as a three dimensional object within the scope of said predetermined theme.

8. The aid according to claim 7, wherein said predetermined theme is selected from the group consisting of sports, nature, pets, fantasy, and combinations thereof.

9. The aid according to claim 7, wherein:
said three dimensional object of the deflector includes integral portions thereof in said indicia of said cap.

10. A method of deflecting the head of a resting infant from reposing upon a preselected area of the head in order to treat or prevent plagiocephaly and torticollis, comprising:
forming a dome-shaped cap of rib knit material, sized to fit an infant-sized head, having an apex defined at the top of the dome shape and having a lower edge defined at the bottom of the dome shape, with a major seam extending from said apex to at least near said lower edge;
forming a longitudinally elongated, arcuate, pliable deflector of a soft material, wherein said deflector is more elongated between the apex and lower edge of the cap and is narrower in a transverse dimension, establishing a deflector that is a positive deterrent to the infant's head from resting on the deflector; and
locating the deflector over said major seam;
attaching the deflector to the cap by incorporating a minor portion of the deflector into the major seam to form a resulting positioning aid for positioning the head of a resting infant;
locating said preselected area of the infant's head; and
applying said positioning aid over the top of the infant's head with the deflector overlying the preselected area of the infant's head to deflect the infant's head from reposing directly on the preselected area.

* * * * *